(12) United States Patent
Brewer et al.

(10) Patent No.: US 12,283,357 B2
(45) Date of Patent: Apr. 22, 2025

(54) SYSTEMS AND METHODS FOR MONITORING USE OF AND ENSURING CONTINUITY OF FUNCTIONALITY OF INSULIN INFUSION PUMPS, GLUCOSE MONITORS, AND OTHER DIABETES TREATMENT EQUIPMENT

(71) Applicant: Bigfoot Biomedical, Inc., Milpitas, CA (US)

(72) Inventors: Jeffrey Brewer, Menlo Park, CA (US); Jon Brilliant, Milpitas, CA (US)

(73) Assignee: BIGFOOT BIOMEDICAL, INC., Milpitas, CA (US)

( * ) Notice: Subject to any disclaimer, the term of this patent is extended or adjusted under 35 U.S.C. 154(b) by 655 days.

(21) Appl. No.: 17/647,112

(22) Filed: Jan. 5, 2022

(65) Prior Publication Data

US 2022/0130506 A1    Apr. 28, 2022

Related U.S. Application Data

(63) Continuation of application No. 15/646,283, filed on Jul. 11, 2017, now Pat. No. 11,238,133.
(Continued)

(51) Int. Cl.
| | |
|---|---|
| *G16H 20/10* | (2018.01) |
| *A61M 5/14* | (2006.01) |
| *A61M 5/168* | (2006.01) |
| *A61M 5/172* | (2006.01) |
| *A61M 5/20* | (2006.01) |

(Continued)

(52) U.S. Cl.
CPC ............. *G16H 20/10* (2018.01); *A61M 5/14* (2013.01); *A61M 5/1723* (2013.01); *A61M 5/20* (2013.01); *G06Q 10/087* (2013.01); *G16H 10/60* (2018.01); *G16H 20/17* (2018.01); *G16H 20/60* (2018.01); *G16H 40/00* (2018.01); *G16H 40/20* (2018.01);
(Continued)

(58) Field of Classification Search
CPC ...................... A61M 5/14; A61M 5/20; A61M 2005/14208; G06Q 10/087
See application file for complete search history.

(56) References Cited

U.S. PATENT DOCUMENTS

| | | |
|---|---|---|
| 5,873,731 A | 2/1999 | Prendergast |
| 8,454,581 B2 | 6/2013 | Estes et al. |

(Continued)

*Primary Examiner* — Paul Danneman
(74) *Attorney, Agent, or Firm* — Goodwin Procter LLP

(57) ABSTRACT

A personal diabetes equipment management system can include at least one diabetes treatment device adapted for use with one or more disposable diabetes devices; a remote server system including an inventory database identifying operational diabetes treatment devices and operational disposable diabetes devices in the possession of a user; and a controller in communication with (i) the at least one diabetes treatment device over a first network connection and (ii) the remote server system over a second network connection, the controller adapted to automatically detect use of the at least one diabetes treatment device and determine an operational condition for the diabetes treatment device or the one or more disposable diabetes treatment devices based on information received from the at least one diabetes treatment device over the first network connection, the controller transmitting update information to the remote server system over the second network connection to update the inventory database.

20 Claims, 8 Drawing Sheets

Related U.S. Application Data

(60) Provisional application No. 62/362,496, filed on Jul. 14, 2016.

(51) Int. Cl.

| | | |
|---|---|---|
| *G06Q 10/087* | (2023.01) | |
| *G16H 10/60* | (2018.01) | |
| *G16H 20/17* | (2018.01) | |
| *G16H 20/60* | (2018.01) | |
| *G16H 40/00* | (2018.01) | |
| *G16H 40/20* | (2018.01) | |
| *G16H 40/40* | (2018.01) | |
| *G16H 80/00* | (2018.01) | |
| *A61M 5/142* | (2006.01) | |

(52) U.S. Cl.
CPC ... *G16H 40/40* (2018.01); *A61M 2005/14208* (2013.01); *G16H 80/00* (2018.01)

(56) References Cited

U.S. PATENT DOCUMENTS

| | | |
|---|---|---|
| 9,848,774 B2 | 12/2017 | Bergstrom et al. |
| 2002/0032582 A1 | 3/2002 | Feeney, Jr. et al. |
| 2005/0277892 A1 | 12/2005 | Chen |
| 2007/0156092 A1 | 7/2007 | Estes et al. |
| 2009/0069787 A1 | 3/2009 | Estes et al. |
| 2009/0118664 A1 | 5/2009 | Estes et al. |
| 2009/0143916 A1 | 6/2009 | Boll et al. |
| 2011/0009724 A1 | 1/2011 | Hill et al. |
| 2014/0309615 A1 | 10/2014 | Mazlish |
| 2016/0098524 A1* | 4/2016 | Himmelstein ......... G16H 40/20 705/2 |
| 2016/0217265 A1 | 7/2016 | Miller et al. |
| 2017/0185733 A1 | 6/2017 | Nogueira et al. |
| 2017/0300931 A1* | 10/2017 | Gerrans ............. G06Q 30/0267 |
| 2018/0107879 A1 | 4/2018 | Laput et al. |
| 2018/0146919 A1 | 5/2018 | Abrams et al. |
| 2023/0074617 A1* | 3/2023 | Valdes ............. A61B 5/150877 |

\* cited by examiner

2000

Deliver to Pharmacy, fax to 1-800-1234, or fill out on-line at www.abc.com
Type One Diabetes Management System Prescription Form

Patient Information (2010)
Name: _____ Gender: M ☐ F ☐ Email: _____
Address: _____ City: _____ State: _____ Zip: _____
Birth Date: _____ Cell #: _____ Home #: _____
Insurance Company: _____ Policy #: _____

Patient Medical Information (2020)
Physician Name: _____ Phone #: _____ Fax #: _____
Address: _____ City: _____ State: _____ Zip: _____
Average Total Daily                Fear of Hypoglycemia: Low ☐ Medium ☐ High ☐
Basal Dose of Insulin: _____ units   [A "low" selection targets lower blood glucose levels.]
Optional Settings: Insulin Sensitivity Factor: _____ Carbohydrate to Insulin Ration: _____

RX ☐  Proscribe the Type 1 Diabetes Management System
       Subscription Length: 1Month Trail ☐  3 Months ☐  6 Months ☐

Subscription Includes: (2030)

| Lease of Durable Diabetes Devices: | Supply of All Your Diabetes Supplies |
|---|---|
| Insulin Pump Controller | • Disposable Pump Bodies<br>• Insulin Cartridges<br>• Infusion Sets:<br>  Select Type: Teflon ☐ Stainless Steel ☐<br>  Select Cannula: 6 mm ☐ 9 mm ☐<br>  Select Tubing: 23 inches ☐ 43 inches ☐ |
| Continuous Glucose Monitor Transmitter | • Disposable CGM Sensors<br>• Additional Accessories:<br>  Select Needs: Skin Wipes ☐ Extra Adhesive Tape ☐ |
| Blood Glucose Meter & Lancing Device | • Test Strips<br>• Control Solution<br>• Lancing needles |
| Select Accessories:<br>• Carrying Case ☐<br>• Backup Mobile Device Battery ☐ | Select Other Supplies:<br>• Ketone Test Strips ☐<br>• Glucose Tablets ☐<br>• Glucagon Emergency Kit ☐ |

(2040)
System Includes Mobile Application and Access to Web Services.
System Requires Patient to have Mobile Device, please select the Operating System: ☐ ☐ ☐ ☐
Mark here if you do not have a Mobile Device running one of the listed operating system: ☐
Authorized By: _____    _____
               Provider's Name [Print] Signature    Date
Complete, sign, and fax to 1-800-1234. You can also scan and email to referals@abc.com. If
You have any questions, call 555-1234. You can also fill this out at www.abc.com

FIG. 2

Insulin Delivery System

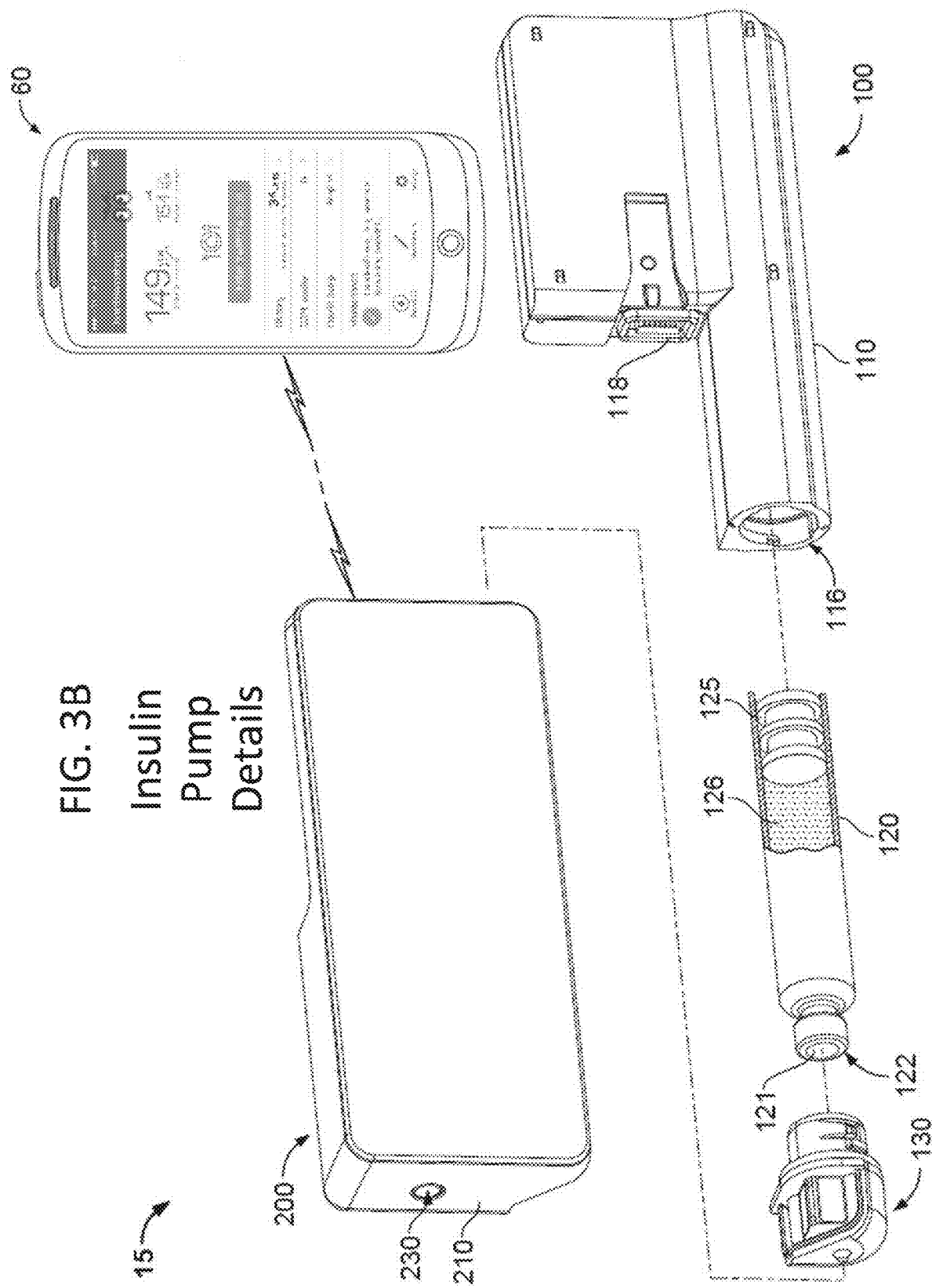

SYSTEMS AND METHODS FOR MONITORING USE OF AND ENSURING CONTINUITY OF FUNCTIONALITY OF INSULIN INFUSION PUMPS, GLUCOSE MONITORS, AND OTHER DIABETES TREATMENT EQUIPMENT

CROSS-REFERENCE TO RELATED APPLICATIONS

This application is a continuation of, and claims priority to, U.S. patent application Ser. No. 15/646,283 filed on Jul. 11, 2017, which claims priority to U.S. Provisional Application Ser. No. 62/362,496, filed on Jul. 14, 2016. The disclosures of the prior applications are considered part of the disclosure of this application, and are incorporated in their entireties into this application.

TECHNICAL FIELD

This document relates to systems and methods for monitoring use and functionality of insulin infusion pumps, glucose monitors, and other diabetes treatment equipment to ensure proper continuity of functionality for such equipment.

BACKGROUND

Insulin infusion pumps and continuous glucose monitors are typically provided to a person with diabetes (PWD) who is insulin dependent as "durable medical equipment" that is intended to be used for a defined length of time. As such, the upfront costs of obtaining an insulin infusion pump and/or a continuous glucose monitor can be high. As such, once a PWD has obtained a continuous glucose monitor and/or an insulin infusion pump, ensuring that the continuous glucose monitor and/or an insulin infusion pump remain in working order and can continuously perform their intended functions is of the utmost importance. In many cases, the burden of identifying a status of such equipment that may interrupt proper, continuous functionality falls upon the PWD. The cognitive burden of continually monitoring the functionality of a continuous glucose monitor and/or an insulin infusion pump to avoid interruptions in the proper functionality of such equipment can place additional stress on the PWD.

SUMMARY

Systems, devices, and methods provided herein can automate monitoring of diabetes treatment equipment through internet-based communication among a number of different computing devices and systems, including specialized computing devices such as insulin pump devices and specifically programmed insulin pump controller devices. For example, insulin pump devices can be configured with various components (e.g., switches, sensors, monitoring devices, and/or other monitoring components) to automatically determine (without user intervention or input) status information related to the functionality of an insulin pump, such as status information (e.g., current amount of remaining insulin), usage information (e.g., amount of insulin dispensed from a cartridge), times when maintenance of an infusion pump device or other diabetes treatment equipment is necessary, the nature of maintenance of an diabetes treatment equipment to be performed, and/or steps to be taken to perform such maintenance. Necessary maintenance activities can be performed, at least in part, in response to such automated monitoring performed by specialized computing devices, such as insulin pump devices and/or insulin pump controller devices.

Automated monitoring and procedures for ensuring continuity of insulin treatment equipment functionality can include communication between various devices across one or more networks, some of which may be private networks (e.g., local area network, virtual private networks) and some of which may be public networks (e.g., internet), using one or more security layers to ensure that the communication, which can include potentially sensitive medical information, remains private and unreadable by potential malicious parties (e.g., man in the middle). For example, one or more sets of encryption keys can be established between each of several computing devices/systems involved in monitoring and maintenance of insulin treatment equipment. Such keys can include symmetric and/or asymmetric encryption keys, and the computing devices/systems can include specialized encryption hardware, such as cryptoprocessors and/or other encryption modules.

Systems, devices, and methods provided herein can reduce the cognitive burden on persons with diabetes (PWDs) or caregivers by providing automated insulin treatment equipment monitoring with automated maintenance functions, including the delivery of diabetes devices and supplies as a service. Systems, kits, and methods provided herein can, in some cases, simplify the procurement process by allowing for order fulfillment through a pharmacy. In some cases, systems, kits, and methods provided herein can include the delivery of a reusable insulin pump controller and a timely supply of disposable insulin pump bodies, infusion sets, and/or prefilled insulin cartridges that are configured to be inserted into the disposable pump bodies, which can all be covered by a single prescription. In some cases, systems, kits, and methods provided herein can include the delivery of a continuous glucose monitoring transmitter (replaced every 3 months) and a timely supply (e.g., automated determination and ordering supplies based on monitoring of supply status by specialized computing devices, which can include predictive ordering in advance of supplies having been depleted) of disposable continuous glucose monitoring sensors that are configured to be removably attached to the continuous glucose monitoring transmitter (replaced every 3 months), which can all be covered by a single prescription. In some cases, systems, kits, and methods provided herein can include the delivery of a reusable blood glucose meter and a timely supply of disposable blood glucose test strips adapted to be inserted into a test strip port in the reusable blood glucose meter, which can all be covered by a single prescription. In some cases, systems, kits, and methods provided herein can include reusable portions of an insulin pump, a continuous glucose monitor, and a blood glucose meter, and at least the necessary disposable diabetes supplies that work with each reusable device as part of a single prescription, which can be set for a predetermined length of time (e.g., 3 months, 6 months, 1 year, etc.). In some cases, systems, kits, and methods provided herein can include the delivery of other diabetes supplies and accessories, such as glucose tablets or gels, insulin pens, backup basal insulin, insulin pen needles, insulin syringes, control solutions for the blood glucose meter, a lancing device, lancets, glucagon emergency kits, ketone strips (for blood or urine), adhesives for the continuous glucose monitor sensors, adhesives for the infusion sets, skin preparation wipes or solutions, adhesive remover, mobile device backup batteries, carrying cases, and sharps containers.

In some cases, systems and methods provided herein can, alternatively or additionally, automatically track the use of both reusable diabetes devices and disposable diabetes supplies to assist a PWD or a caregiver with the reordering of diabetes supplies. For instance, specialized computing devices (e.g., insulin pump devices, insulin pump controllers) can be configured with components (e.g., sensors, monitoring devices) to automatically track the use of reusable diabetes devices and disposable diabetes supplies. System and methods provided herein can, in some cases, estimate a remaining inventory of diabetes devices and supplies in the PWD's custody (i.e., a personal inventory) and reserve, with one or more remote server systems, a virtual inventory of diabetes devices and supplies for shipment to the PWD prior to when one or more diabetes supplies and/or supplies are depleted from the personal inventory. Virtual inventory can be represented on the server side and/or the client side using one or more data structures identifying a variety of details regarding the inventory, such as a SKU for the inventory, order numbers, shipment tracking information, expected date of delivery, and/or other details. In some cases, methods and systems provided herein can estimate a personal inventory based on a recommended usage pattern, a usage pattern particular to the PWD, an average usage pattern for typical PWDs, or based on activities detected by the system. Such usage patterns can be determined using any of a variety of appropriate techniques, such as machine learning techniques (e.g., neural networks, supervised learning techniques, unsupervised learning techniques, clustering techniques) that can generate usage models across one or more devices and supplies for a particular user. For example, in some cases a reusable insulin pump controller can use one or more specifically located components (e.g., sensors, monitoring devices) to detect replacement of an insulin cartridge, a disposable insulin pump body, and/or a change of the infusion set. In some cases, a continuous glucose monitor transmitter can detect changes of the continuous glucose monitor sensor. In some cases, systems provided herein can detect each blood glucose measurement taken using the blood glucose meter to determine a number of remaining blood glucose test strips, such as through active and/or passive monitoring (e.g., wireless monitoring, wired monitoring) of the blood glucose meter's operations and/or communication.

In some cases, methods and systems provided herein can use activity information, which can be detected by specialized computing devices with one or more particularly designed sensors and/or monitoring components, as a proxy for use of disposable devices. For example, in some cases, methods and systems provided herein can assume that an adhesive for a continuous glucose monitor is changed at least when the continuous glucose monitor sensor is changed, which may be detected using one or more sensors and/or monitoring component that are positioned on or around a continuous glucose monitor. In some cases, systems provided herein can permit a PWD or a caregiver to input information related to the use of a diabetes supply. For example, systems provided herein can permit a PWD or a caregiver to input the injection of outside insulin or the administration of glucagon, which can be assumed to be from an insulin pen or a glucagon emergency kit respectively.

Systems and methods provided herein can, in some cases, include a user interface displaying both the estimated personal inventory and a virtual inventory for each diabetes device and/or supply, a planned ship date for the virtual inventory, an ability for the PWD or a caregiver to modify the number of diabetes devices or supplies in their personal inventory, and an ability for the PWD to modify the items ordered for the next delivery and/or the ship date for the virtual inventory. For example, a insulin controller device, which may have a smaller form factor display, can output a graphical user interface (GUI) that is specifically configured to dynamically resize and reposition information in the GUI, such as estimated virtual and personal inventory information as well as control features for modifying that information, depending on dynamically adjusted display parameters (e.g., device orientation, user selected zoom level, text/font size, display size, extended display vs. primary display). For instance, such GUI features can be dynamically adjusted in terms of size and position so that the information is visible and not overlapping, and/or so that a user will not have to scroll laterally across a screen, but instead can scroll vertically to view information. Such dynamic adjustment can take place, for instance, in response to determining that one or more portions of the GUI features are or would be overlapping/obscured based on the display parameters.

Methods provided herein can include (a) receiving a physician written prescription for a diabetes supplies service that includes an insulin infusion pump and/or a continuous glucose monitor; (b) processing the prescription (e.g., through a pharmacy); (c) sending a PWD an insulin infusion pump and/or a continuous glucose monitor and other associated diabetes medical supplies; (d) tracking the use of insulin and/or other associated diabetes medical supplies; and (e) determining when and/or what additional insulin and/or other additional associated diabetes medical supplies should be delivered to the PWD, where the additional delivery of insulin and/or other additional associated diabetes medical supplies is within the scope of the physician written prescription. Methods provided herein can additionally include a process of submitting a claim for reimbursement through an insurance company, a government agency, or other third-party payer. Methods provided herein can, in some cases, include a collection of a co-pay and/or billing an insurance company, a government agency, or other third-party payer. Methods provided herein can, in some cases, include contacting the person with diabetes to register and/or train the PWD in how to properly use the insulin infusion pump, the continuous glucose monitor, or a system including both the insulin infusion pump and the continuous glucose monitor. Methods provided herein can, in some cases, include sending additional insulin and/or other additional associated diabetes medical supplies to the PWD and optionally collecting a co-pay and billing an insurance company, a government agency, or other third-party payer for the continued use of the diabetes supply service and/or for the additional insulin and/or other additional associated diabetes medical supplies. Methods provided herein can additionally submit the prescription for renewal to a physician to continue the supply of additional insulin, replacement insulin infusion pumps, replacement continuous glucose monitors, and/or additional associated diabetes medical supplies.

Systems and devices provided herein can track the use of insulin and/or other associated diabetes medical supplies and/or estimate when additional insulin and/or other additional associated diabetes medical supplies will be needed by a person with diabetes. In some cases, systems and devices provided herein can include an inventory management system. In some cases, the inventory management system can include both an estimated personal inventory (e.g., diabetes supplies in the PWD's possession) and a virtual inventory (e.g., a list of diabetes supplies reserved for shipment to the PWD). In some cases, systems and devices provided herein can detect maintenance activities and dynamically update the inventory management system.

In one implementation, a personal diabetes supplies management system includes at least one diabetes device, the at least one diabetes device being adapted to be used with one or more disposable diabetes supplies; a remote server system including an inventory database identifying operational diabetes devices and operational disposable diabetes supplies in the possession of a user; and a controller in communication with (i) the at least one diabetes device over a first network connection and (ii) the remote server system over a second network connection, the controller being adapted to automatically detect use of the at least one diabetes device and determine an operational condition for the at least one diabetes device or the one or more disposable diabetes supplies based, at least in part, on information received from the at least one diabetes device over the first network connection, the controller transmitting update information to the remote server system over the second network connection to update the inventory database to reflect the number of operational diabetes devices and supplies in the possession of the user.

Such an implementation can optionally include one or more of the following features. The at least one diabetes device can be an insulin pump, a continuous glucose monitor, a blood glucose meter, or a smart insulin pen. The disposable diabetes supplies can be selected from the group consisting of drugs, cartridges including drugs, disposable insulin pump components, infusion sets, blood glucose meter test strips, and disposable glucose meter sensors for continuous glucose monitors. The controller can be a smart phone with (i) a first wireless chipset to wirelessly communicate with the at least one diabetes device over the first network connection and (ii) a second wireless chipset to wirelessly communicate with the remote server system over the second network connection and over the internet. The controller can include a display that is programmed to output alerts in a graphical user interface presented on the display, the alerts being output to the person with diabetes about a personal diabetes supplies inventory condition. The controller's display can be further programmed to display a recommendation to the person with diabetes identifying the supplies that the person with diabetes should procure in order to maintain an appropriate personal diabetes supplies inventory. The controller can be further programmed to output one or more selectable input features in association with the recommendation in the graphical user interface to permit a person with diabetes to accept the recommendation to have the identified supplies shipped to the person with diabetes. The controller can be further programmed to output one or more graphical elements in the graphical user interface to permit the person with diabetes to make modifications to a list of the identified supplies and place an order on the controller for a modified list of diabetes supplies.

The controller can be programmed to output one or more selectable user input features in a graphical user interface to allow a person with diabetes to indicate that one or more diabetes supplies has been used, damaged, or destroyed. The controller can be programmed to receive and display information regarding reimbursement policies of one or more third-party payers for the person with diabetes, wherein the controller is programmed to display a recommendation to the person with diabetes identifying the supplies that the person with diabetes should procure in order to maintain an appropriate personal diabetes supplies inventory, the recommendation being based in part on the reimbursement policies. The reimbursement policies can include a time period for when diabetes supplies can be ordered and reimbursed, a maximum number of a type of diabetes supply that can be reimbursed, reimbursement rates, and a list of reimbursed supplies. The controller can be further programmed to display in a graphical user interface a cost to the person with diabetes for ordering the identified diabetes supplies. The controller can be further programmed to output a list the identified diabetes supplies with corresponding graphical interface elements to permit the user to alter the list of the identified diabetes supplies, wherein the controller is programmed to dynamically update the displayed cost for the list as the user alters the list in the graphical interface elements. The remote server system can be programmed to reorder and ship additional diabetes devices, parts, or medication to the person with diabetes, charge the person with diabetes and/or a third-party payer, and update the inventory database in response to each shipment. The controller can be programmed to output in a graphical user interface a query to the person with diabetes to determine if a shipment has arrived. The controller can be programmed to display package tracking data in a graphical user interface for each shipment of additional diabetes devices, parts, or medication.

In another implementation, a method of providing diabetes devices and supplies includes (a) receiving, at a computer system, a physician written prescription for a diabetes supplies service that includes at least one diabetes device; (b) processing, by the computer system, the prescription; (c) causing, by the computer system, at least one diabetes device to be sent to a user, the at least one diabetes device being adapted to be used with one or more disposable diabetes supplies and one or more of the disposable diabetes supplies; (d) tracking, by the computer system and through (i) communication between the computer system and a controller device over a first network connection and (ii) communication between the controller device and the at least one diabetes device over a second network connection, use of the at least one diabetes device to determine an operational condition for the at least one diabetes device or the one or more disposable diabetes supplies; and (e) generating and transmitting, by the computer system and to a client device associated with the user, information about a personal diabetes inventory condition for diabetes devices and/or diabetes supplies delivered to the person with diabetes.

Such an implementation can optionally include one or more of the following features. Generating and transmitting the information to the client device about the personal diabetes inventory condition can include recommending a reorder of additional diabetes supplies. The method can further include causing, by the computer system, additional diabetes supplies to be delivered to the user, wherein the additional delivery of diabetes supplies is within the scope of the physician written prescription. The method can further include submitting, by the computer system, a claim for reimbursement for the additional diabetes supplies through an insurance company, a government agency, or other third-party payer. The method can further include collecting, by the computer system, a co-pay from user for the additional diabetes supplies. The method can further include submitting, by the computer system, the prescription for renewal to a physician prior to delivering the additional diabetes supplies to the user. The method can further include contacting, by the computer system, the user to register and/or train the user in how to properly use the at least one diabetes device. Transmitting the information to the client device can cause the client device to display the personal diabetes inventory on a user interface of the client device. The user interface can permit the user to update a number of the one or more disposable diabetes supplies. The user interface can prompt the user to provide comments on why the user is updating the number of the one or more disposable diabetes supplies. The user interface can further displays a virtual inventory of items to be shipped at an upcoming ship date and an indication of when those items will be shipped. The method can further include receiving, at the computer system, updates to the personal inventory based on changes made through the user interface on the client device; and updating, by the computer system, the virtual inventory in response to the changes to the personal inventory.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 depicts an exemplary prescription form.

FIG. 3B depicts the exemplary reusable controller, disposable pump body, insulin cartridge, and infusion set of FIG. 3A.

Like reference symbols in the various drawings may indicate like elements.

DETAILED DESCRIPTION OF ILLUSTRATIVE EMBODIMENTS

Figure 1:
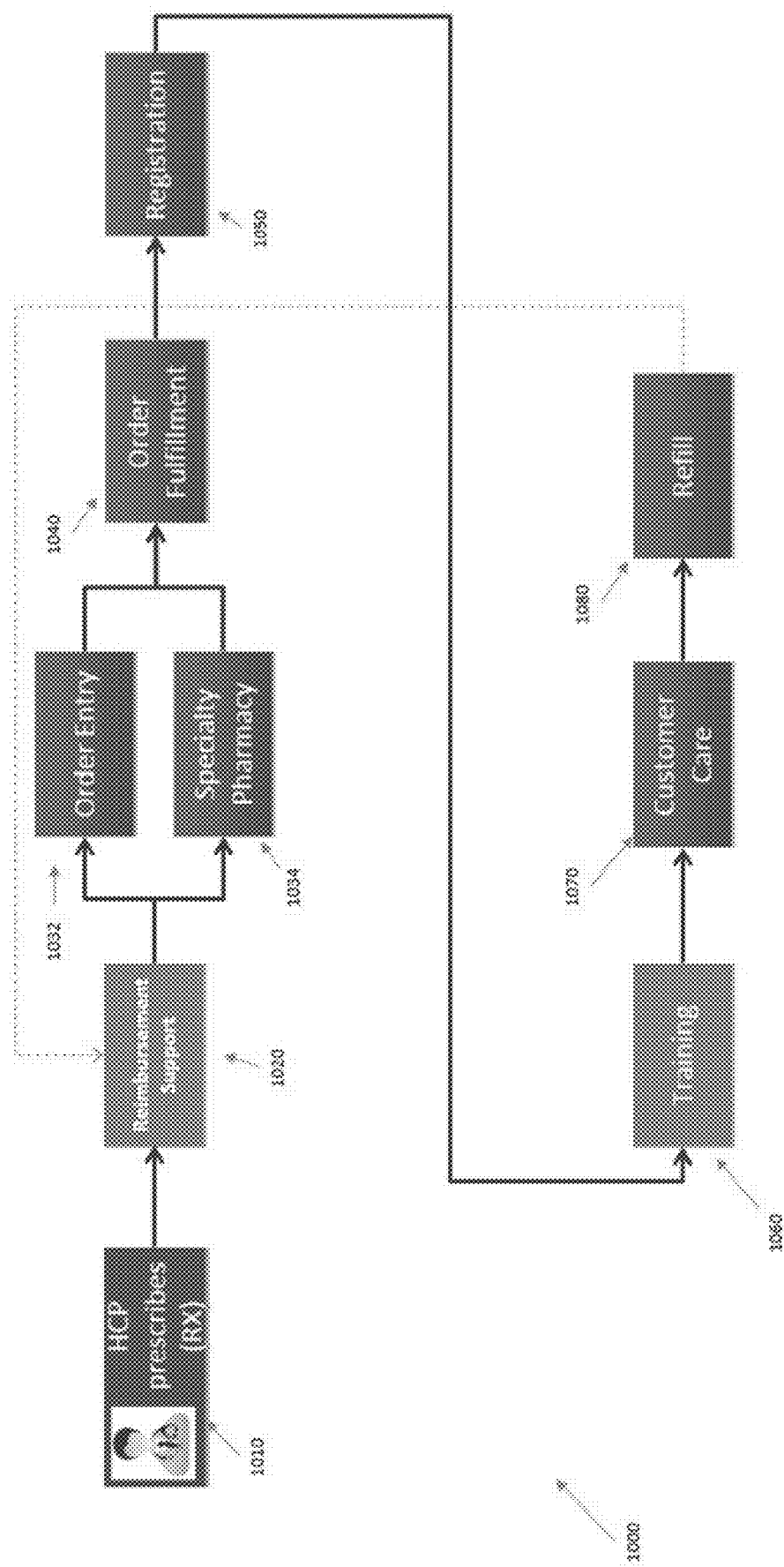
FIG. 1 depicts a flowchart showing a diabetes equipment maintenance process-.

Methods and systems described herein enable a diabetes treatment system to automatically identify when maintenance or service procedures may be necessary to ensure continuity of functionality of the diabetes treatment system and to automatically obtain diabetes treatment equipment or supplies that may be required to ensure proper continued functionality of the diabetes treatment system. This can be facilitated, for example, through specialized computing devices (e.g., insulin pump device, insulin pump controller device) that are configured with particularly placed sensing/monitoring components (e.g., sensors) to automatically monitor and determine supply information (e.g., supply usage, current supply status). Such monitoring can be used to automatically reorder equipment/supplies from a remote server system in a secure manner so that transmissions over one or more networks are not detectable apart from the endpoints of the communication, such as through the use of symmetric and/or asymmetric encryption techniques. Such automatic monitoring and ordering of diabetes supplies can reduce the time, the paperwork, and the cognitive burden for a person with diabetes (PWD), the PWD's caregivers, the PWD's physician, and/or the PWD's insurance provider. In some cases, methods and systems provided herein can treat the delivery of diabetes supplies to a PWD as a service with a fixed or variable cost. For example, in some cases, a diabetes supplies service provided herein can include an insulin pump, at least one blood glucose measurement device, and all of the associated diabetes supplies that a PWD might use for a fixed monthly fee. In some cases, methods and systems provided herein can include an inventory management system that can track (using specialized computing devices with sensors and/or other monitoring components) the use and/or expiration of diabetes supplies and ensure that the PWD or a caregiver receives refills of diabetes supplies in a timely manner. In some cases, systems, devices, and methods provided herein can track usage, expiration dates, and/or maintenance activities to estimate a remaining personal inventory of diabetes supplies and/or update a list of items to be shipped on a future date, such as through the use of predictive analytics based on current and historical supply usage data for a PWD. In some cases, systems and devices provided herein can be automatically connected to and authenticated with one or more cloud computer systems (or other server systems) to enable diabetes supplies to be reordered (and optionally shipped) with a minimal amount of interaction with the PWD or the PWD's caregiver. In some cases, methods and systems provided herein can include a prescription from a physician that is fulfilled through a pharmacy (e.g., a brick and mortar establishment or a direct order system). In some cases, methods and systems provided herein can collect a copay (e.g., a monthly copay) for the diabetes supplies service and/or include reimbursement support. The methods and systems provided herein can improve the functionality of a diabetes treatment system by ensuring that proper components/supplies necessary to provide continuous functionality of the diabetes treatment system are available when needed.

Referring to FIG. 1, a diabetes supply system 1000 can begin with a physician prescribing 1010 the diabetes supplies service. In some cases, the prescription can be submitted by the physician electronically via a web portal for an electronic health record/electronic medical record (EHR/EMR) system. In some cases, the prescription can be handwritten and delivered to a pharmacy by the PWD. In some cases, systems and methods provided herein can generate information pamphlets on the diabetes supplies service and/or prescription templates for PWDs or caregivers to print and bring to a physician. In some cases, a PWD or a caregiver can download a mobile application that demonstrates to the PWD, a caregiver, and/or a physician how the diabetes supplies service functions and explain how the physician can prescribe the diabetes supplies service. In some cases, a mobile application or web service for the diabetes supplies service can provide an estimation of how much the diabetes supplies service will cost the PWD or the PWD's caregiver based on the PWDs insurance and/or usage of diabetes supplies. In some cases, the periodic cost (e.g., monthly cost) of the diabetes supplies service can be fixed, which can be based on an insulin usage of the PWD, an expected usage of other diabetes supplies, and/or the types of diabetes supplies included in the diabetes supply service prescribed by the physician. In some cases, a fixed monthly cost can be set without regard to an expected usage rate. In some cases, an initial cost can be equal to the periodic cost. In some cases, the initial cost and the periodic cost of the diabetes supplies service can be variable based upon the supplies actually delivered. In some cases, a fixed monthly cost to the PWD or the PWD's caregiver and/or the insurance company can be updated after two or more payment periods based on the actual use.

In some cases, an exemplary prescription form can resemble form 2000 as depicted in FIG. 2, which can include a PWD identification section 2010, a PWD medical information section 2020, a service program selection section 2030, and a physician signature section 2040. In some cases, form 2000 can be physically printed and hand signed by physician for delivery to a pharmacy. In some cases, the physically printed prescription can include a fax number for faxing the completed form to a pharmacy. In some cases, the prescription form can recommend that the PWD fill out PWD identification section 2010. Section 2010 can include the PWD's name, gender, mailing address, e-mail address, telephone number (e.g., home, cell, and/or work), and insurance information. Section 2020 can include the name of the PWD's physician, the physician's contact information, and request information indicating how the PWD's diabetes should be treated (e.g., an average total daily basal dose, a fear of hypoglycemia rating, an insulin sensitivity factor, an insulin-to-carbohydrates ratio, and/or other user-specific parameters that might dictate therapy (e.g., weight, average total daily insulin). In some cases, information about how the PWD should be treated might be in a separate section from the information about the PWD's physician. In some cases, the prescription form can ask for information about the type of diabetes and/or the past treatment of the PWD. In some cases, the prescription form can indicate that certain user-specific parameters are optional. In some cases, PWD medical information section 2020 can ask a physician to enter an average total daily basal insulin amount and/or a total daily insulin amount input for entering by the physician. In some cases, the PWD medical information section 2020 can instruct the physician to enter a fear of hypoglycemia input after consulting with the PWD. In some cases, the PWD medical information can allow the physician to enter an insulin to carbohydrate ratio and/or an insulin sensitivity factor for the PWD if available, but indicate that entry of these variables are optional as they can be estimated based on the total daily basal insulin amount and/or the total daily insulin amount. In some cases, a service program selection section 2030 can indicate a length of time for the prescription for the diabetes supply service. In some cases, the service program selection can include check boxes for the physician to indicate that the service is prescribed and to indicate the preferences for different supplies. For example, in some cases, section 2030 can ask the physician, a caregiver, and/or the PWD to indicate the type or types of insulin, the type or types of infusion sets, optional types of pumps, optional types of blood glucose meters, optional types of continuous glucose meters, optional types of insulin pens and/or insulin syringes, and optional types of other diabetes supplies included in the service.

Additionally and/or alternatively, the form 2000 can be electronic and displayed on a GUI of a physician's computing device and/or a PWD's computing device. The form 2000 can be presented in a GUI as part of an application, webpage, and/or other software code that is being executed (locally and/or remotely) for presentation on the computing device. The sections 2010-2040 can be electronically fillable, such as through one or more input devices (e.g., keyboard, microphone, stylus, touchscreen). One or more portions of the sections 2010-2040 can be auto-populated with suggested information for the PWD, which may be confirmed through the GUI. The GUI can be configured to dynamically adjust so that it is displayed consistently across different computing devices with different display parameters, and can be configured to dynamically adjust the sizing, spacing, and/or positioning of the sections 2010-2040 within the GUI so that each of the sections 2010-2040 are visible (not obscured). The GUI can include input devices through which the physician signature section 2040 can be securely and authentically signed by the physician, such as through voice recognition and/or biometric scanning techniques (e.g., fingerprint scanner, optical identity recognition) to verify the physician's identity. Once authorized, the form 2000 can be submitted over one or more networks to a computer system to process the form 2000. Referring back to FIG. 1, after the physician has prescribed the diabetes supplies service, the prescription can be reviewed for reimbursement support 1020 to determine the costs to the PWD and/or one or more reimbursement entities (e.g., insurance companies, Medicare, Medicaid, etc.). In some cases, form 2000 can be filled out using a web portal and the web portal can output an expected cost to the PWD or a caregiver based on the information included in the form using reimbursement support 1020 to review the entered insurance information, the selected service, and/or the expected amount of insulin use. The reimbursement support 1020 can be provided as part of a computer system that automatically and/or manually reviews the form 2000 to determine whether the form 2000 satisfies one or more applicable rules for the PWD, insurance provider, and/or other interested parties. In some cases, a PWD or a caregiver can obtain an estimate of a monthly cost using a mobile application or web portal where the PWD or a caregiver enters the same information. In some cases, a web portal and/or mobile application used by the PWD, a caregiver, or the physician can provide real-time cost estimates and/or insurance reimbursement information for a variety of different service packages. For example, in some cases, certain insurance programs may cover services that include select diabetes supplies but not cover services that include other diabetes supplies.

Once the costs to the PWD and/or one or more reimbursement entities are determined, the order is entered 1032, optionally through a specialty pharmacy 1034, the copay or total payment collected, and the order fulfilled 1040. When the order is entered 1032, the cost to the PWD is collected (e.g., electronic funds transfer, electronic credit/debit to account), optionally by a specialty pharmacy 1034. In some cases, credit card or other payment information can be collected and optionally retained by the pharmacy for future periodic payments (e.g., monthly payments). Such information can be stored using one or more secure storage techniques, such as encryption, obfuscation, and/or information bifurcation across various storage locations. In some cases, methods and systems provided herein can cause the user's computing device to output a GUI prompt for the user to confirm a copay payment and the order (e.g., on a web portal, via an e-mail, or using a mobile device).

Additionally, upon the PWD seeking to fulfill the service prescription by providing the payment or copay, a determination of the initial supplies and quantities needed for the PWD will be automatically determined based upon the expected usage patterns, reorder delivery time period, and/or permitted usage and reorder parameters for the PWD, insurance provider, and/or prescription service. For example, the total daily insulin amount can determine an estimated rate of insulin use by the PWD. In some cases, the initial quantities of supplies delivered by the service can depend upon the particular requirements of the insurance companies that insure the PWD, which may govern how often the PWD should receive additional diabetes supplies. For example, some insurance programs may require refill orders take place no less than 30 days apart or no less than 90 days apart. In some cases, the PWD can set the reorder delivery time period. In some cases, the reorder delivery time period will be every month. In some cases, the reorder delivery time period will be every 90 days. In some cases, the reorder delivery time period can be variable based on the PWD's diabetes supply inventory. Information on the PWD's diabetes supply inventory can be automatically collected by one or more components of a diabetes treatment system, such as the pump controller or a handheld device in communication with the pump controller.

Order fulfillment 1040 can be satisfied by a brick and mortar pharmacy, via a mail order specialty pharmacy, or by a medical device manufacturer or distributor. In some cases, an initial delivery can include a delivery kit including both reusable components and disposable diabetes supplies. Delivery via mail (or other delivery techniques, such as by drone and/or other autonomous vehicles) can include providing a PWD with one or more updates as to the progress of the delivery, like tracking information that can be presented in real-time on a GUI of the PWD's computing device. Updates can be provided at various intervals, such as when the delivery is a threshold time period (e.g., 5 minutes, 15 minutes, 30 minutes, 1 hour) from arriving at the destination. Such updates can be provided, for example, via push notification that cause the PWD's computing device to output the notification in the GUI, and can include a selectable link that the PWD can select to view the progress of the delivery in real-time, such as the current location of the delivery superimposed over a map (along with information identifying the destination, the estimated time of arrival, and the route being travelled). Various techniques can be used to alert a PWD even when the PWD's computing device is offline, such as through notifying a secondary/alternative computing device for the PWD that can receive the notification, queue it for transmission to the PWD's computing device, and transmit the notification (possibly over an alternate communication connection with the PWD's computing device, such as a short range communication connection) to the PWD's computing device to cause the notification to be delivered to the PWD's computing device while it is otherwise inaccessible via the internet. Such notifications can be beneficial to a PWD, who may be receiving supplies that need special handling and/or treatment to ensure that they are usable. A discussion of exemplary diabetes supplies that can be delivered in an initial delivery are discussed below in regard to FIGS. 3A-3G.

After or concurrently with the order entry 1032 and order fulfillment 1040, the PWD or the PWD's caregiver can register 1050 with the diabetes supplies service to ensure that the PWD or the PWD's caregiver is adequately informed about the diabetes supplies service and/or how to use the particularly delivered diabetes supplies. In particular, registration can permit the PWD or the PWD's caregiver to receive training 1060 to view and/or correct an inventory management system, interact with customer care system 1070, and reorder diabetes supplies 1080. In some cases, the PWD or the PWD's caregiver can register using a web portal, a mobile application, near-field communication (NFC) transmission of PWD or PWD caregiver information/authorization to an NFC receiver connected to a computing device/computer system to automatically enroll a PWD, other short-range wireless communication (e.g., Bluetooth, Wi-Fi) of PWD or PWD caregiver information/authorization for registration, or by mailing or faxing a registration form. In some cases, devices or systems included in the diabetes supplies service can require that the PWD or the PWD's caregiver complete training modules and/or pass a course quiz prior to using those devices or systems. For example, in some cases, an insulin pump delivered as part of the diabetes supplies service can require that the PWD or a caregiver practice using the insulin pump before actually using the insulin pump to deliver insulin to the PWD. In some cases, a mobile application or web portal can be used to display training videos, and/or to communicate with an insulin pump device and/or insulin pump controller device to verify proper usage of the devices by the user as part of one or more training modules. In such training instances, the insulin pump device and/or the insulin pump controller device can operate in a training mode that simulates actual operation of the devices to prompt user responses and actions, which can be compared to model/correct responses and actions to determine whether a PWD has passed the training to begin using the devices.

Once the PWD or a caregiver has completed training 1060, the PWD or caregiver can additionally access an inventory management system or customer care system 1070 as long as the PWD or the PWD's caregiver continues to subscribe to the diabetes supplies service. The inventory management system or customer care system 1070 can be a remote server system (e.g., cloud based computer system) that is accessed via a mobile application for a smartphone, a web portal usable with any internet-connected computer, and/or via telephone. The inventory management system and customer care system/service 1070 can require authentication of a PWD's identity before providing access to patient data, such as through username/password verification, biometric verification, voice verification, facial recognition, and/or other authentication techniques/challenges. Customer care system 1070 can allow the PWD to access or update account data, physician data, insurance information, record incidents, and/or respond to surveys.

In some cases, as discussed below in regards to FIG. 4, customer care system 1070 can include a GUI including both a personal inventory features and a virtual inventory features that can be output concurrently and combined in the same GUI view. In some cases, inventory management system can automatically keep the PWD or a caregiver updated in real-time about their usage patterns and remaining supply and prompt the user to reorder needed supplies (or can automatically reorder such supplies when, for instance, the user has preauthorized such automatic reorders). For example, inventory management systems can provide alerts and notifications to a PWD and/or caregiver's computing device, such as push notifications, regarding status, reorder suggestions/confirmations, automatically placed reorders, and/or other relevant information. As discussed above, various techniques can be used to provide such notifications to a PWD and/or caregiver's computing device when the device is offline, such as through communication with a secondary/alternative computing device. In some cases, a PWD or caregiver can enter information into an insulin pump or a handheld device configured to control an insulin pump to indicate to the inventory management system they have used or disposed of a diabetes supply. In some cases, a PWD or caregiver can use their computing device to provide updates to the inventory management system with an updated count for each delivered diabetes supply. In some cases, devices and systems provided herein can automatically track usage and/or maintenance activities to automatically estimate a remaining count of the diabetes supplies. For example, one or more sensors on an insulin pump can detect when an insulin cartridge is removed and a new insulin cartridge inserted, and/or detect the amount of insulin left in a cartridge installed in the insulin pump. In some cases, refill 1080 can occur automatically based on when the inventory management system indicates that supplies are running low and/or at regular periodic intervals, with the specifically delivered supplies for a refill being determined by the inventory management system.

In some cases, methods, devices, and systems provided herein can store and track expiration dates of one or more diabetes supplies. In some cases, some diabetes supplies actually expire before a user can exhaust them. For example, glucagon may have a 12 month lifespan, and certain PWDs may not use glucagon during that lifespan. In another example, ketone strips may be provided in a vial have a 6 month lifespan, and a PWD may not use all of the ketone strips during that lifetime. In another example, insulin may be in a form where it must be discarded 30 days after opening, thus some methods, systems, and devices provided herein can track when diabetes supplies expire based on a date of opening or accessing that diabetes supply (e.g., an insulin cartridge used in a backup pen may be partially used prior to its expiration). Additionally, infusion sets, disposable pump bodies, and blood glucose meter test strips can all have expiration dates. In some cases, methods, systems, and devices provided herein can alert a user to the presence of expired diabetes supplies and automatically reorder a sufficient inventory of diabetes supplies prior to their expiration. In some cases, methods, systems, and devices provided herein can suggest the use of diabetes supplies in a particular order based on upcoming expiration dates in order to reduce waste. In some cases, methods, systems, and devices provided herein can generate reports regarding the use or accumulation of expired/unused diabetes supplies to determine a medication-therapy adherence score.

In some cases, methods and systems provided herein can permit a PWD or a caregiver to procure a diabetes management system starter kit including both reusable diabetes devices and a number of disposable diabetes supplies via a pharmacy system or the like so that the PWD or a caregiver can simply pay a relatively small fee at the pharmacy window to obtain the diabetes devices and supplies without burdensome applications, reimbursement requests, or other time-consuming paperwork. Also, the PWD may experience less delay between the time of the prescription and the time of starting therapy using the diabetes management system because the paperwork burdens normally imposed upon the PWD or the PWD's caregiver and the treating physician (e.g., paperwork required for preauthorization of "durable medical equipment") may be eliminated or reduced. Furthermore, the distribution systems and methods described herein, which can include a subscription price per a regular time interval (e.g., a monthly subscription price), may provide relief to health insurance providers by reducing and simplifying the costs for treating diabetes.

Figure 3A:
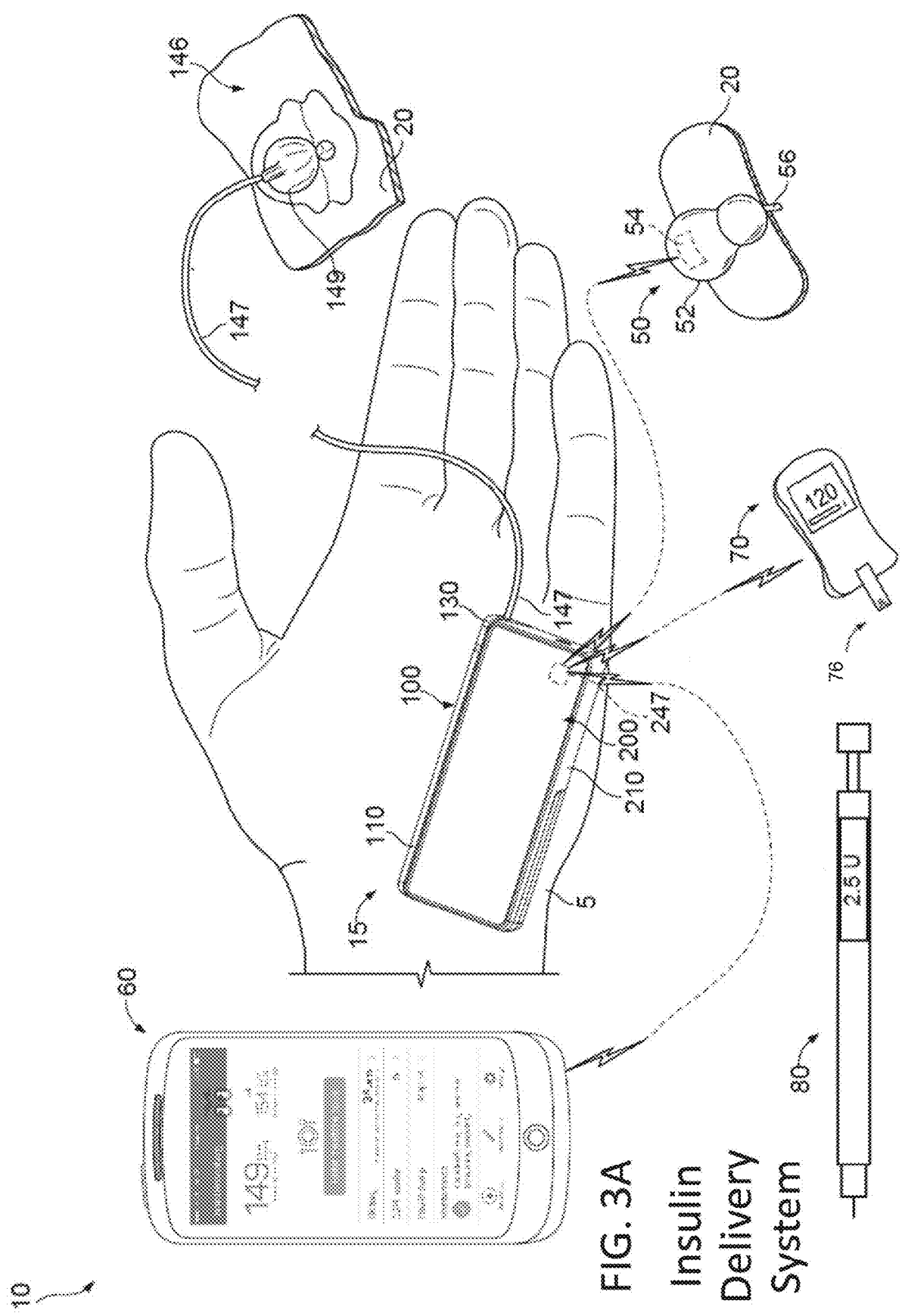
FIG. 3A depicts components of an exemplary diabetes treatment management system, which includes components that can be supplied via a diabetes supplies service delivery process provided herein.
Figure 3C:
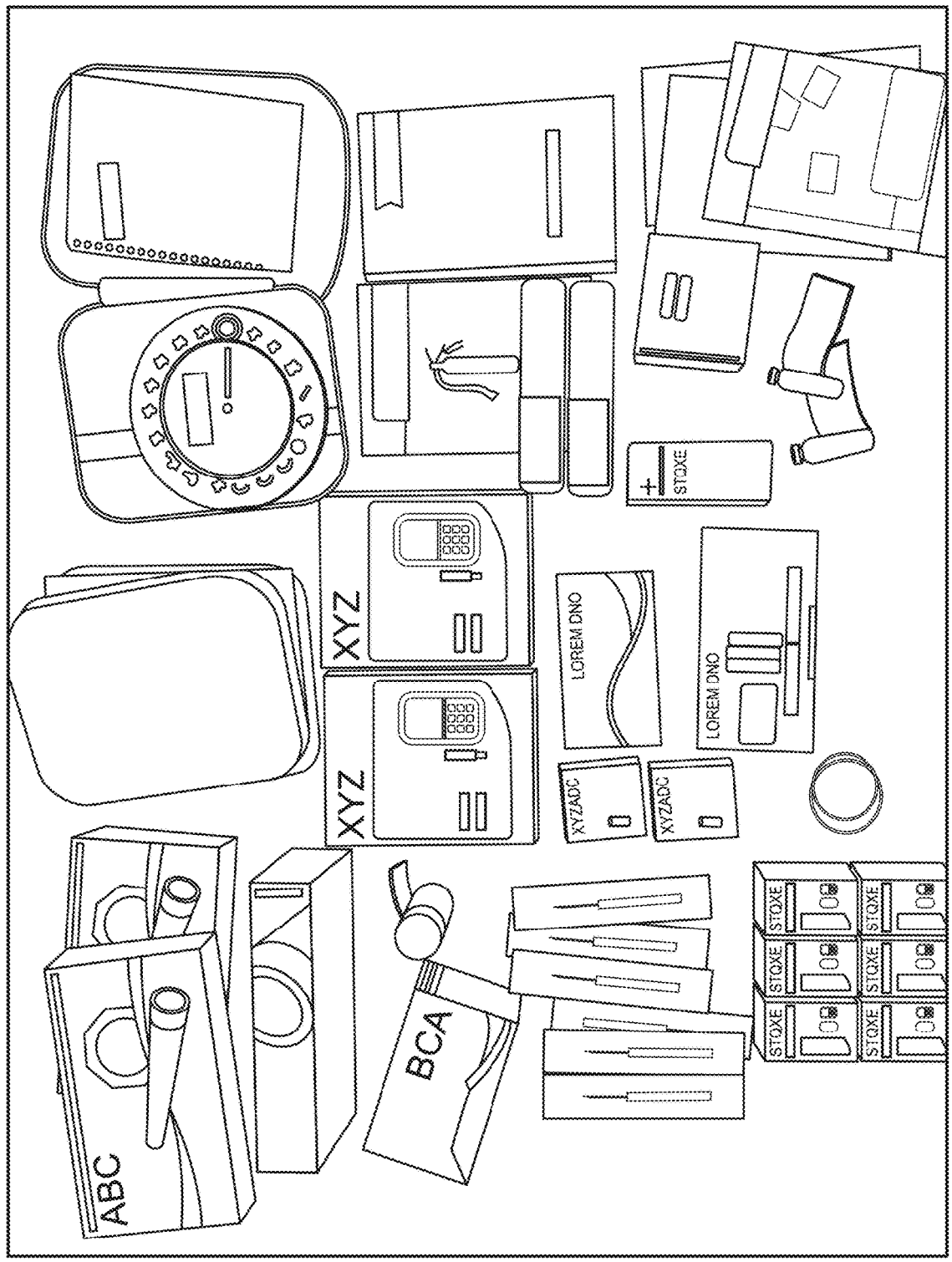
FIGS. 3C-3G depict exemplary diabetes supplies.

In some cases, methods and systems provided herein can include a system including connected diabetes devices and a plurality of disposable diabetes supplies. FIG. 3A depicts an exemplary connected diabetes system 10, which includes a pump assembly 15 featuring a disposable insulin pump body 100 and a reusable insulin pump controller 200, a continuous glucose monitor 50 featuring a reusable continuous glucose monitor transmitter 52 and a disposable continuous glucose monitor sensor 56, and a blood glucose meter 70 that uses disposable blood glucose test strips 76. As shown, controller 200, blood glucose meter 70, and continuous glucose monitor transmitter 52 can all communicate wirelessly. Additionally, system 10 can also include a mobile device 60, in wireless communication with one or more components of system 1. In some cases, system 10 is connected to a remote server in the cloud (e.g., via mobile device 60). System 10 can additionally include an insulin pen 80 and/or insulin syringes (not depicted). In some cases, an insulin pen 80 can be a smart insulin pen that can also have wireless communication with one or more components of system 1. FIG. 3A also depicts an infusion set 147 connected to pump assembly 15. Additional details about how system 10 can be used are discussed below. In some cases, systems and methods provided herein can use the components of the pump assembly 15, such as sensors and other monitoring components of the pump body 100 and/or the mobile device 60, to automatically detect use of diabetes supplies to determine whether an item shipped to the PWD or caregiver should be removed from a personal inventory. For example, insulin usage can be automatically tracked by the pump assembly 15 to determine an amount of insulin left in the PWD's personal inventory. In some cases, system 10 can prompt the user to inform the system regarding infusion set changes and use that information to update a number of infusion sets remaining in a personal inventory. In some cases, system 10 can detect a number of blood glucose meter uses, including invalid attempts, to update a number of blood glucose test strips remaining in a personal inventory. For example, blood glucose meter 70 can use one or more sensors/mechanisms to automatically detect each time a blood glucose test strip 76 is entered into the meter 70 even if it does not result in a valid blood glucose reading, and meter 70 can communicate (e.g., wirelessly communicate in real-time, communicate test strips used over a period of time) to controller 200 a number of blood glucose test strips used prior to a valid blood glucose reading being achieved. In some cases, systems and methods can detect changes to the continuous glucose monitor sensor (e.g., electrical changes related to the sensor, like impedance values changing more than a threshold amount or falling outside of an approved range) to update a number of continuous glucose monitor sensors remaining in the personal inventory.

Exemplary insulin pump assembly 15, as shown, can include reusable pump controller 200 and a disposable pump body 100, which can contain a reservoir for retaining insulin. A drive system for pushing insulin out of the reservoir can be included in either the disposable pump body 100 or the reusable pump controller 200 in a controller housing 210. Reusable pump controller 200 can include a wireless communication device 247, which can be adapted to communicate with a wireless communication device 54 of continuous glucose monitor 50, a mobile device 60, a blood glucose meter 70, and other diabetes devices in the system (e.g., a smart pen 80), such as those discussed below. In some cases, insulin pump assembly 15 can be sized to fit within a palm of a hand 5. Insulin pump assembly 15 can include an infusion set 146. Infusion set 146 can include a flexible tube 147 that extends from the pump body 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the drug dispensed through tube 147 passes through the cannula 149 and into the user's body. The cap device 130 can provide fluid communication between an output end of an insulin cartridge (not shown) and tube 147 of infusion set 146. In some cases, reusable pump controller 200 can detect when a new disposable pump body 100 is attached to the controller 200. In some cases, each disposable insulin pump body can include memory including identification information, and controller 200 can record that ID, transmit the ID through mobile device 60 to an inventory management system (using secure transmission techniques, such as end to end encryption) at a remote server to indicate that a particular disposable insulin pump has been at least partially used and remove it from a personal inventory for the PWD. Such signals can be transmitted in real-time (transmitted on demand and when network connections are available) and/or can be delayed until at appropriate times when permitted by the pump assembly 15 and/or the mobile device 60 so as to not jeopardize PWD safety. For example, the pump assembly 15 and/or the mobile device 60 can include safety layers that are embedded within their operating systems/kernels that act as gateways for operations of secondary importance (not related to immediate PWD health and safety) to be delayed until times when critical processing, monitoring, therapy, and/or other operations/communication regarding the immediate health and well-being of the PWD is not underway. By delaying such communications (e.g., storing them in a queue of messages/packets of secondary importance for transmission during non-critical periods of operation by the assembly 15 and/or the device 60), the technical performance of the system 10 with regard to providing stable and reliable insulin delivery to the PWD can be improved.

In some cases, controller 200 can detect when a new cap device 130 is connected to the pump assembly 15, for example, through the use of one or more sensors, chips, electrical connections, and/or other monitoring components that can physically, electrically, magnetically, and/or optically detect the new cap device being connected (other ways of detecting the new cap device 130 are also possible). In some cases, controller 200 can detect when a new infusion set is connected to the pump assembly 15, for instance, through the use of one or more sensors, chips, electrical connections, and/or other monitoring components that can physically, electrically, magnetically, and/or optically detect the new cap device being connected (other ways of detecting the new infusion set is connected are also possible). Such detections can cause the controller 200 and the pump assembly to transmit (in real-time) one or more signals to the mobile computing device 60, which may retransmit and/or aggregate the information for production to a remote server system. In some cases, mobile computing device 60 can inform a user about the need to change an infusion set and prompt, such as through a GUI for the device 60, the user to indicate that the infusion set 147 has been changed.

Continuous glucose monitor 50 can include a housing, a wireless communication device 54, and a sensor shaft 56. The wireless communication device 54 can be contained within the housing and the sensor shaft 56 can extend outward from the housing. In use, the sensor shaft 56 can penetrate the skin 20 of a user to make measurements indicative of the PWD's blood glucose level or the like. In some cases, the sensor shaft 56 can measure glucose or another analyte in interstitial fluid or in another fluid and correlate that to blood glucose levels. In response to the measurements made by the sensor shaft 56, the glucose monitoring device 50 can employ the wireless communication device 54 to transmit data to a corresponding wireless communication device 247 housed in the pump system 15. In some cases, the monitoring device 50 may include a circuit that permits sensor signals (e.g., data from the sensor shaft 56) to be communicated to the communication device 54. The communication device 54 can transfer the collected data to the controller device 200 (e.g., by wireless communication to the communication device 247). Alternatively, the monitoring device 50 can employ other methods of obtaining information indicative of a PWD's blood glucose levels and transferring that information to the controller device 200. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. In some cases, continuous glucose monitor 50 can detect when a new sensor 56 is secured to the housing, and communicate that a new sensor has been used to a remote server (e.g., through controller 200 and mobile device 60). In some cases, a particular sensor 56 can be IDed and the ID sent to a remote server. In some cases, mobile device 60 can inform a user about the need to change sensor 56 and prompt the user to indicate that the sensor 56 has been changed.

Diabetes management system 10 may optionally include a blood glucose meter 70. In some cases, blood glucose meter 70 can be in wireless communication with reusable pump controller 200. Blood glucose meter 70 can take a blood glucose measurement using one or more test strips 76 (e.g., blood test strips). A test strip can be inserted into a strip reader portion of the glucose meter device 70 and then receive the PWD's blood to determine a blood glucose level for the user. In some cases, the glucose meter device is configured to analyze the characteristics of the user's blood and communicate (e.g., via a Bluetooth wireless communication connection) blood glucose information (and optionally information about a number of test strips used) to the controller device 200. The blood glucose meter 70 can be manually operated by a user and may include an output subsystem (e.g., display, speaker) that can provide the user with blood glucose readings that can be subsequently entered into the controller or user interface to collect the data from an unconnected BGM into the system. In some cases, a user can manually input a glucose meter reading, and methods and systems can assume that each entered blood glucose reading consumed 1 (or more) test strips. In some cases, methods and systems provided herein can assume a ratio of unusable or spoiled test strips for every valid blood glucose reading. The blood glucose meter 70 can, in some cases, automatically transmit (over wired and/or wireless connections) information about test strip usage and/or blood glucose readings to the controller 200, the mobile device 60, and/or other components of the system 10.

Optionally, system 10 may include a bolus administering device 80 (e.g., syringe, an insulin pen, a smart syringe with device communication capabilities, or the like) through which bolus dosages can be manually administered to a PWD. In some cases, a suggested dosage for a bolus to be administered using the bolus administering device 80 can be output to a user via the user interface of the controller device 200 and/or the user interface of the mobile computing device 60. In some cases, the bolus administering device 80 can automatically communicate through a wired and/or wireless connection with the controller device 200 and/or the mobile computing device 60. In some cases, system 10 can allow users to input insulin deliveries made using a syringe or insulin pen, which can then be used to change an inventory for insulin from insulin pens. In some cases, a PWD can have an emergency supply of long-lasting insulin (e.g., Lantus insulin), and methods and systems provided herein can automatically detect when a supply of insulin has been used, for instance, when the PWD is detached from the insulin pump for a predetermined length of time (e.g., at least 10 hours, at least 12 hours, at least 18 hours, or at least 24 hours).

FIGS. 3A-3G all depict diabetes devices and diabetes supplies that can be included in diabetes supply services provided herein. In FIG. 3B, details regarding a specific infusion pump system 15 are depicted. As shown in FIG. 3B, a particular infusion pump system can include a reusable insulin pump controller 200 and a disposable insulin pump body 100 that receives an insulin cartridge 120, which is secured in the disposable insulin pump body 100 with a cap 130 prior to being secured to controller 200. In some cases, cap 130 is attached to an infusion set (such as infusion set 147 of FIG. 3A). Methods and systems provided herein can include a lease (e.g., a monthly lease) of controller 200 and a regular supply of disposable insulin pump bodies 100, insulin cartridges 120, and caps 130 (optionally attached to an infusion set). Additional details about the devices shown in FIG. 3B are discussed below.

Figure 3E:
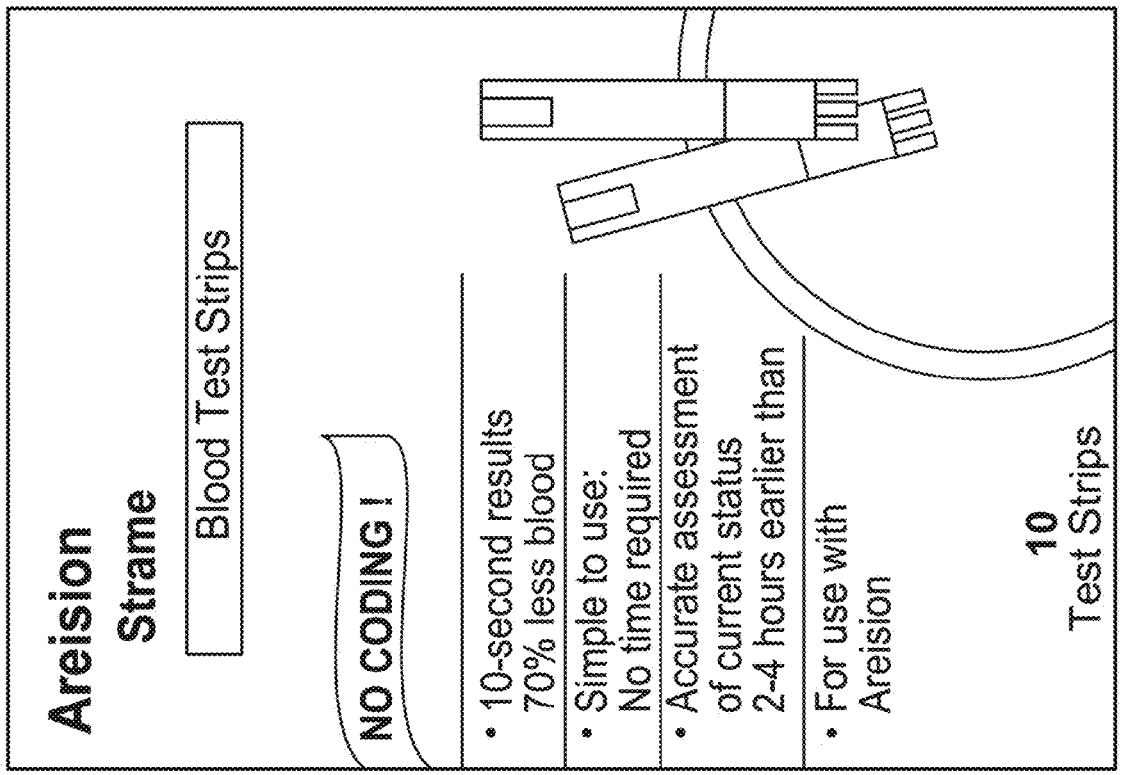
Figure 3D:
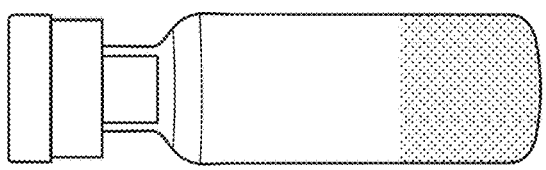
Figure 3F:
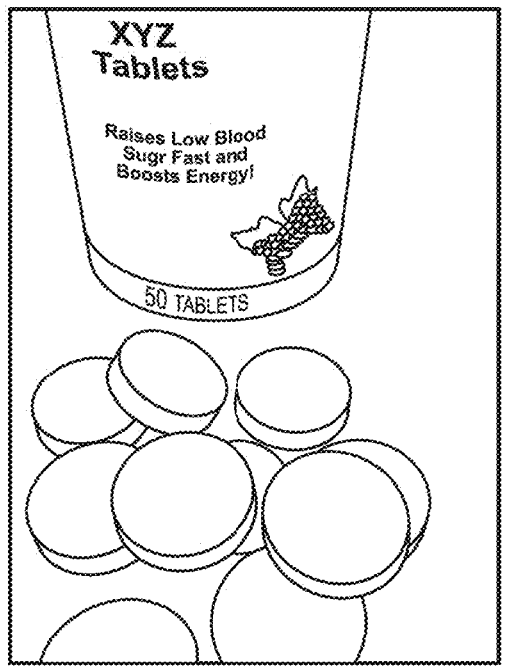
Figure 3G:
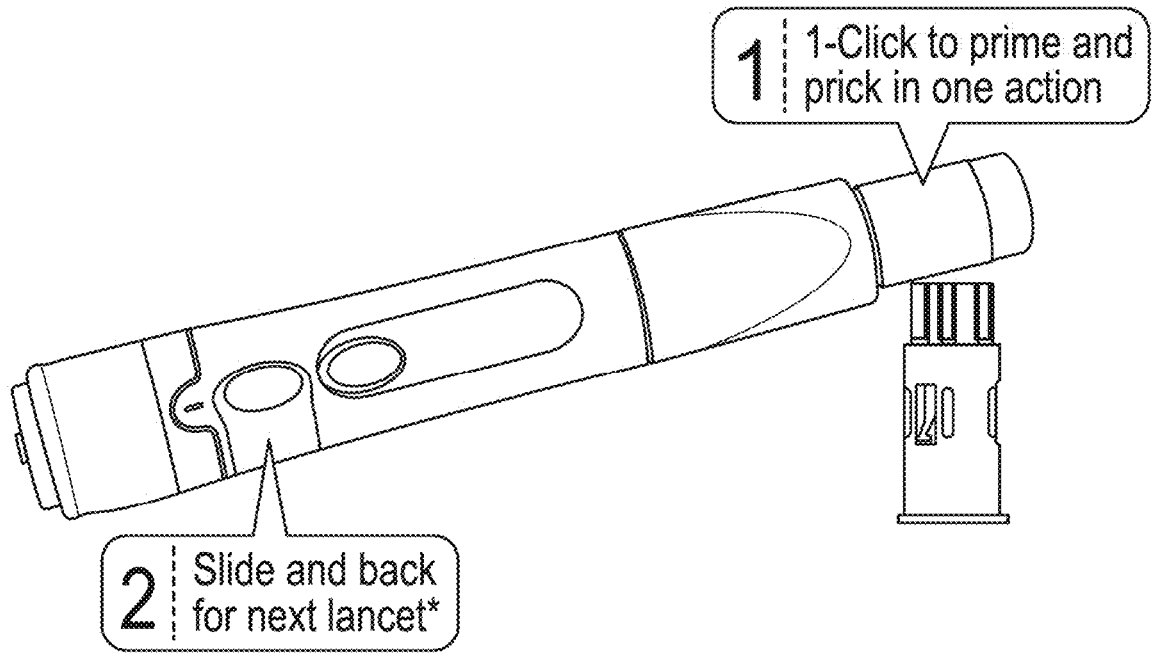

FIGS. 3C-3G depict an exemplary assortment of commercially available diabetes devices and supplies that can be delivered to a PWD or caregiver using methods and systems provided herein. FIG. 3D depicts a vial of powdered glucagon, which can be included in a glucagon emergency kit along with a syringe loaded with a liquid. FIG. 3E depicts a package of ketone test strips. FIG. 3F depicts glucose tablets. FIG. 3G depicts a lancing device and a lancing needle set.

Figure 4:
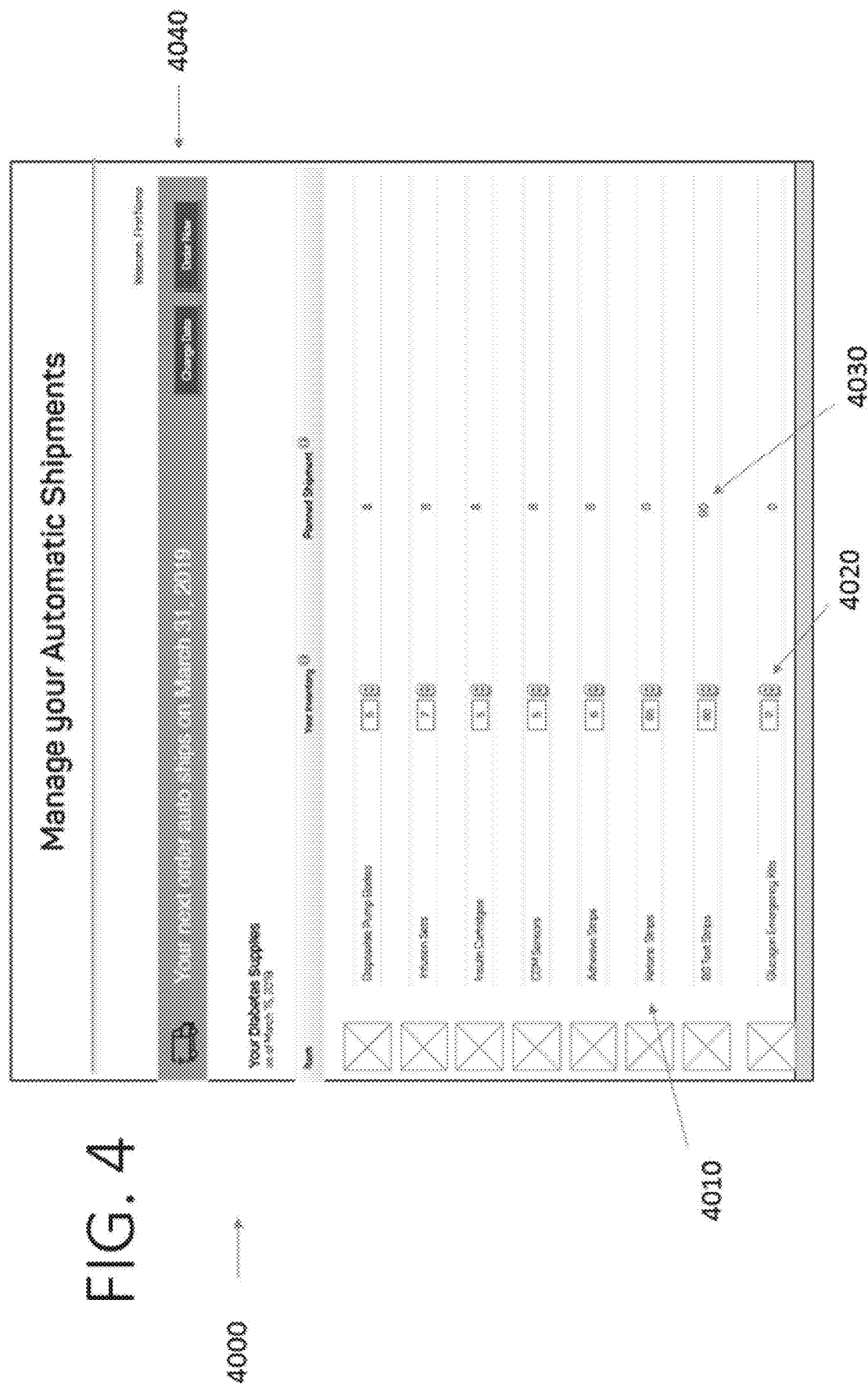
FIG. 4 depicts a first exemplary inventory management user interface.

FIG. 4 depicts an exemplary inventory management user interface 4000 (e.g., GUI), which has graphical display elements that include a list of disposable diabetes devices 4010, a series of estimates of the number of each type of supply in a personal inventory 4020, a number of items to be included in a next shipment in a virtual inventory 4030, and an indication of the next shipping date 4040. The list of items to be included can include a name of each type of supply and/or a picture of each type of supply. In some cases, a PWD or caregiver can add or change preferences for types of supplies to be delivered to the PWD or caregiver. For example, in some cases, a PWD or caregiver can select a particular type of ketone test strip. In some cases, the types of supplies to be delivered to the PWD or caregiver can be automatically populated based on a prescription that is processed for a PWD, such as through the form 2000 described above in FIG. 2. A PWD or caregiver may be prompted to confirm addition of one or more automatically identified supplies before they are formally added to the types of supplies to be delivered to the PWD or caregiver.

Personal inventory 4020 can include automatically generated, real-time estimates regarding a number of each supply remaining in the PWD's or a caregiver's possession. As discussed above, such estimates can be generated based on the automatic supply monitoring performed by the components of the system 10 and reporting of the results of the supply monitoring, which may be done in real-time. In some cases, each number can include a user selectable toggle switch to allow the PWD or a caregiver to update the number of each supply listed. In some cases, a PWD or caregiver can be prompted to comment on or provide other indications why the system might have an inaccurate estimate of the personal inventory for that supply. For example, a PWD or caregiver altering the current inventory can be provided with a selectable list of possible reasons why the estimate was inaccurate, such as supplies were lost, unusable as delivered, and/or not yet used.

In some cases, inferences can be drawn that the estimates are accurate when the PWD or caregiver views the GUI 4000 and does not alter any of the estimates in the personal inventory 4020. Such inferences may be weighted based on factors that may indicate how closely the PWD or caregiver analyzed the estimates in the personal inventory 4020, such as through an amount of time the user views the GUI 4000 (e.g., dwell time on the personal inventory 4020 information). The longer a user views the GUI 4000 without changing any of the estimates, the more likely that estimate is accurate and the higher the accuracy of that estimate can be weighted. A variety of techniques can be used to make these determinations, such as client-side code (e.g., javascript, mobile app code) that stops and starts timers when the user is viewing the GUI 4000 (e.g., the GUI 4000 has focus), identifies whether values of the personal inventory 4020 are changed, and reports that information back to a remote system.

Virtual inventory 4030 can inform the user of supplies reserved, ordered, and/or in transit/available for the PWD. The virtual inventory 4030 can be updated based on changes to the personal inventory. In some cases, the number of items for each subsequent delivery can be based on the packaging of multiple devices into a single package. The GUI 400 also includes an indication of when the next shipment will be delivered 4040. Such features around the virtual inventory 4030 and delivery of orders 4040 can build trust with the PWD or caregiver to reduce stress associated with being concerned regarding whether the PWD will have sufficient diabetes supplies going forward. In some cases, the user interface 4000 can include buttons to allow the PWD or caregiver to change the shipping date or request a prompt delivery. In some cases, a shipping date can automatically change in response to changes to personal inventory 4020.

As described above, the GUI 4000 can additionally include one or more features to permit the GUI 4000 to be visually reproduced in a similar manner (to have the same look and feel) across different devices (e.g., mobile devices, desktop/laptops) and display environments (e.g., mobile app, web browser, different display sizes, different display orientations). The GUI 4000 can be produced with dynamic code that is provided to and executed/interpreted by the client device to automatically adjust the GUI 4000 so that the features 4010-4040 have the same look and feel across different devices. For example, the code to implement the GUI 4000 can detect whether the elements 4010-4040 are overlapping or otherwise not being presented within one or more display parameters, and can dynamically adjust the sizing, spacing, and/or position of the elements 4010-4040 so that each of the elements 4010-4040 are visible and displayed within the one or more display parameters.

Referring back to FIGS. 3A and 3B, the reusable insulin pump controller 200 can electrically communicate with disposable insulin pump body 100 to control a drive system housed in disposable insulin pump body 100 to dispense a drug to a user (e.g., through a tube 147 of an infusion set 146 in this example). When reusable insulin pump controller 200 and disposable insulin pump body 100 are assembled together, the user can (in some embodiments) conveniently wear diabetes management system 10 against the user's skin under clothing, in a pouch clipped at the waist, or in the user's pocket while receiving the drug dispensed from disposable insulin pump body 100.

Briefly, in use, disposable insulin pump body 100 in this embodiment is configured to removably attach to reusable insulin pump controller 200 in a manner that provides a secure fitting, an overall compact size, and a reliable electrical connection. For example, as described in more detail below in connection with FIG. 3B, reusable insulin pump controller 200 can include a housing 210 having a number of features that mate with complementary features of the pump housing 110. In such circumstances, reusable insulin pump controller 200 can removably attach with disposable insulin pump body 100 in a generally side-by-side configuration. The compact size permits the pump assembly 15 to be discreet and portable. Reusable insulin pump controller 200 can receive user input for purposes of operating diabetes management system 1.

Continuous glucose monitor 50 can include reusable transmitter 52, a wireless communication device 54 in reusable transmitter 52, and a disposable sensor shaft 56. In use, the sensor shaft 56 can penetrate the skin 20 of a user to make measurements indicative of characteristics of the user's blood or interstitial tissue fluid (e.g., the user's blood glucose level or the like). In response to the measurements made by the sensor shaft 56, continuous glucose monitor 50 can employ the wireless communication device 54 to transmit data to a corresponding wireless communication device 247 housed in connected diabetes system 10. In some embodiments, continuous glucose meter 50 may include a circuit that permits sensor signals (e.g., data from the sensor shaft 56) to be communicated to the communication device 54. The communication device 54 can transfer the collected data to reusable insulin pump controller 200 (e.g., by wireless communication to the communication device 247). Alternatively, continuous glucose meter 50 can employ other methods of obtaining information indicative of a user's blood characteristics and transferring that information to reusable insulin pump controller 200. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level. Furthermore, it should be understood that in some alternative embodiments, continuous glucose meter 50 can be in communication with reusable insulin pump controller 200 via a wired connection.

In particular embodiments, diabetes management system 10 can further include the mobile computing device 60 that can communicate with reusable insulin pump controller 200 through a wireless and/or wired connection with reusable insulin pump controller 200 (e.g., via a Bluetooth wireless communication connection in this particular embodiment). The mobile computing device 60 can be any of a variety of appropriate computing devices, such as a smartphone, a tablet computing device, a wearable computing device, a smartwatch, a fitness tracker, a laptop computer, a desktop computer, and/or other appropriate computing devices. The mobile computing device 60 can receive and log data that is collected by reusable insulin pump controller 200, such as blood glucose readings, dosage delivery information, and also can receive user inputs (e.g., user-selected parameters to be stored on reusable insulin pump controller 200, user-confirmation of bolus dosages (described below), and others). In some embodiments, the mobile computing device 60 provides a user interface (e.g., graphical user interface (GUI), speech-based user interface, motion-controlled user interface) through which users can provide information to control operation of reusable insulin pump controller 200 and diabetes management system 1. For example, the mobile computing device 60 can be a mobile computing device running a mobile app that communicates with reusable insulin pump controller 200 over short-range wireless connections (e.g., Bluetooth connection, Wi-Fi Direct connection) to provide status information for diabetes management system 10 and allow a user to control operation of diabetes management system 10 (e.g., toggle between delivery modes, adjust settings, log food intake, confirm/modify/cancel bolus dosages, and the like).

Diabetes management system 10 may optionally communicate with blood glucose meter 70 in addition to (or as an alternative to) continuous glucose meter 50. For example, one or more test strips 76 (e.g., blood test strips) can be inserted into a strip reader portion of the glucose meter device 70 to be tested for characteristics of the user's blood when a blood sample is taken into the strip. The glucose meter device is configured to analyze the characteristics of the user's blood and communicate (e.g., via a Bluetooth wireless communication connection) the information to reusable insulin pump controller 200. The blood glucose meter 70 can be manually operated by a user and may include an output subsystem (e.g., display, speaker) that can provide the user with blood glucose readings. The blood glucose meter 70 may be configured to communicate data (e.g., blood glucose readings and invalid attempts at making blood glucose readings) obtained to reusable insulin pump controller 200 and/or other devices, such as the mobile computing device 60. Such communication can be over a wired and/or wireless connection, and the data can be used by reusable insulin pump controller 200 and/or the mobile computing device 60 to perform multiple delivery modes and/or a secondary feedback loop for diabetes management system 1.

Referring now to FIG. 3B, disposable insulin pump body 100 in this embodiment includes a housing structure 110 that defines a cavity 116 in which a fluid cartridge 120 can be received. Disposable insulin pump body 100 also can include a cap device 130 (which may be part of an infusion set) to retain the fluid cartridge 120 in the cavity 116 of the housing structure 110. Disposable insulin pump body 100 can include a drive system (e.g., including a battery powered actuator, a gear system, a drive rod, and other items that are not shown in FIG. 2) that advances a plunger 125 in the fluid cartridge 120 so as to dispense fluid therefrom. In this embodiment, reusable insulin pump controller 200 communicates with disposable insulin pump body 100 to control the operation of the drive system. Optionally, reusable insulin pump controller 200 may be configured as a reusable component that provides electronics and a user interface to control the operation of disposable insulin pump body 100. In such circumstances, disposable insulin pump body 100 can be a disposable component that is disposed of after a single use. For example, disposable insulin pump body 100 can be a "one time use" component that is thrown away after the fluid cartridge 120 therein is exhausted. Thereafter, the user can removably attach a new pump body (having a new fluid cartridge inserted) to the reusable controller device 200 for the dispensation of fluid from a new fluid cartridge. Accordingly, the user is permitted to reuse reusable insulin pump controller 200 (which may include complex or valuable electronics, as well as a rechargeable battery) while disposing of the relatively low-cost pump body 100 after each use. Such a pump assembly 15 can provide enhanced user safety as a new pump body (and drive system therein) is employed with each new fluid cartridge.

The pump assembly 15 can be a medical infusion pump assembly that is configured to controllably dispense a drug from the cartridge 120. As such, the fluid cartridge 120 can contain a drug 126 to be infused into the tissue of a targeted individual, such as a human or animal patient. For example, disposable insulin pump body 100 can be adapted to receive a fluid cartridge 120 in the form of a carpule that is preloaded with insulin or another drug for use in the treatment of Diabetes (e.g., exenatide (BYETTA, BYDUREON) and liraglutide (VICTOZA), pramlintide (SYMLIN), or others). Such a cartridge 120 may be supplied, for example, by Eli Lilly and Co. of Indianapolis, IN. Other examples of drugs that can be contained in the fluid cartridge 120 include: pain relief drugs, hormone therapy, blood pressure treatments, anti-emetics, osteoporosis treatments, or other injectable drugs. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the drug is injected or otherwise received).

In some embodiments, disposable insulin pump body 100 can include one or more structures that interfere with the removal of the fluid cartridge 120 after the fluid cartridge 120 is inserted into the cavity 116. For example, the pump housing structure 110 can include one or more retainer wings (not shown) that at least partially extend into the cavity 116 to engage a portion of the fluid cartridge 120 when the fluid cartridge 120 is installed therein. Such a configuration may facilitate the "one-time-use" feature of disposable insulin pump body 100. In some embodiments, the retainer wings can interfere with attempts to remove the fluid cartridge 120 from disposable insulin pump body 100, thus ensuring that disposable insulin pump body 100 will be discarded along with the fluid cartridge 120 after the fluid cartridge 120 is emptied, expired, or otherwise exhausted. In another example, the cap device 130 can be configured to irreversibly attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, disposable insulin pump body 100 can operate in a tamper-resistant and safe manner because disposable insulin pump body 100 can be designed with a predetermined life expectancy (e.g., the "one-time-use" feature in which the pump device is discarded after the fluid cartridge 120 is emptied, expired, or otherwise exhausted).

Still referring to FIG. 3B, reusable insulin pump controller 200 can be removably attached to disposable insulin pump body 100 so that the two components are mechanically mounted to one another in a fixed relationship. In some embodiments, such a mechanical mounting can also form an electrical connection between the removable controller device 200 and disposable insulin pump body 100 (for example, at electrical connector 118 of disposable insulin pump body 100). For example, reusable insulin pump controller 200 can be in electrical communication with a portion of the drive system (as shown) of disposable insulin pump body 100. In some embodiments, disposable insulin pump body 100 can include a drive system that causes controlled dispensation of the drug or other fluid from the cartridge 120. In some embodiments, the drive system incrementally advances a piston rod (not shown) longitudinally into the cartridge 120 so that the fluid is forced out of an output end 122. A septum 121 at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device 130 to the housing structure 110. Thus, when disposable insulin pump body 100 and reusable insulin pump controller 200 are mechanically attached and thereby electrically connected, reusable insulin pump controller 200 communicates electronic control signals via a hardwire-connection (e.g., electrical contacts along connector 118 or the like) to the drive system or other components of disposable insulin pump body 100. In response to the electrical control signals from reusable insulin pump controller 200, the drive system of disposable insulin pump body 100 causes a drug to incrementally dispense from the fluid cartridge 120. Power signals, such as signals from a battery (not shown) of reusable insulin pump controller 200 and from the power source (not shown) of disposable insulin pump body 100, may also be passed between reusable insulin pump controller 200 and disposable insulin pump body 100.

Still referring to FIG. 3B, reusable insulin pump controller 200 can include a user interface that permits a user to monitor and (optionally) control the operation of disposable insulin pump body 100. In this depicted embodiment, the user interface of reusable insulin pump controller 200 may not include physical buttons, but it includes at least a display device and a collection of icons that can be illuminated to convey information regarding the current state of operation for the pump assembly 10. For example, the icons can indicate whether the assembly 15 is on, the current mode of operation (e.g., closed-loop mode, open-loop mode), whether there are pending notifications or other information for the user to review, whether user input is required, whether reusable insulin pump controller 200 is wirelessly connected with the mobile computing device 60 (or other computing devices), and/or other notifications. Optionally, the display screen of the user interface may be in the form of a touch screen in which a touch-sensitive layer is positioned over the LCD screen component. Additionally or alternatively, the mobile computing device 60 may provide a more full-featured user interface for purposes of receiving user input (which is then communicated to reusable insulin pump controller 200 via the wireless communication connection) and providing more detailed information displays. For example, as described in more detail below, the user may view and interact with the user interface of the mobile computing device 60 (e.g., an interface of the mobile app configured to work with the pump assembly 10) to shuffle through a number of menus or program screens that show particular operational modes (e.g., closed-loop delivery mode and open-loop delivery mode), settings (e.g., user-specific dosage parameters) and data (e.g., review data that shows the drug dispensing rate, the total amount of drug dispensed in a given time period, the amount of drug scheduled to be dispensed at a particular time or date, the approximate amount of drug remaining in the cartridge 120, or the like). In this alternative example, the user can adjust the modes and/or settings, or otherwise program reusable insulin pump controller 200 by touching one or more virtual buttons (or physical buttons) on the user interface of the mobile computing device 60. For example, the user may press one or more of the virtual buttons (or physical buttons) on the user interface of the mobile computing device 60 to change the operation of diabetes management system 10 from a closed-loop delivery mode to an open-loop delivery mode. In some implementations, the display device of the controller, the display of the mobile computing device 60, or both may also be used to communicate information regarding remaining battery life. Optionally, reusable insulin pump controller 200 may be equipped with additional components, such as one or more of the following: motion sensors (not shown), secondary light instruments 230, vibratory output devices (not shown), a microphone to obtain voice input, and the like.

In some alternative embodiments, the user interface can be equipped with one or more user-selectable buttons so that the user can press one or more of the buttons to shuffle through a number of menus or program screens that show particular operational modes (e.g., closed-loop delivery mode and open-loop delivery mode), settings (e.g., user-specific dosage parameters) and data (e.g., review data that shows the drug dispensing rate, the total amount of drug dispensed in a given time period, the amount of drug scheduled to be dispensed at a particular time or date, the approximate amount of drug remaining in the cartridge 120, or the like).

Referring again to FIGS. 3A and 3B, the pump assembly 15 can be configured to be portable and can be wearable and concealable. For example, a user can conveniently wear the pump assembly 15 against the user's skin (e.g., skin adhesive) underneath the user's clothing or carry the pump assembly 15 in the user's pocket (or other portable location) while receiving the drug dispensed from disposable insulin pump body 100. The pump assembly 15 depicted in FIG. 3A as being held in a user's hand 5 so as to illustrate its size in accordance with some embodiments. This embodiment of the pump assembly 15 is compact so that the user can wear the portable pump assembly 15 (e.g., in the user's pocket, connected to a belt clip, adhered to the user's skin, or the like) without the need for carrying and operating a separate module. In such embodiments, the cap device 130 of disposable insulin pump body 100 can be configured to mate with an infusion set 146. In general, the infusion set 146 can be a tubing system that connects the pump assembly 15 to the tissue of the user (e.g., to deliver a drug into the tissue under the user's skin). The infusion set 146 can include a flexible tube 147 that extends from a cap device 130 or disposable insulin pump body 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue of the user so that the drug dispensed through the tube 147 passes through the cannula 149 and into the user's body. The cap device 130 can provide fluid communication between the output end 122 (FIG. 3B) of the fluid cartridge 120 and the tube 147 of the infusion set 146.

In some embodiments, the pump assembly 15 can be pocket-sized so that disposable insulin pump body 100 and controller device 200 can be worn in the user's pocket or in another portion of the user's clothing. In some circumstances, the user may desire to wear the pump assembly 15 in a more discrete manner. Accordingly, the user can pass the tube 147 from the pocket, under the user's clothing, and to the infusion site where the adhesive patch can be positioned, or in an accessory case clipped or hooked to the clothing (not shown), or by means of an attached accessory clip (not shown). As such, the pump assembly 15 can be used to deliver drug to the tissues of the user in a portable, concealable, and discrete manner.

In some embodiments, the pump assembly 15 can be configured to adhere to the user's skin directly at the location in which the skin is penetrated for drug infusion. For example, a rear surface of disposable insulin pump body 100 can include a skin adhesive patch so that disposable insulin pump body 100 can be physically adhered to the skin of the user at a particular location. In these embodiments, the cap device 130 can have a configuration in which the drug passes directly from the cap device 130 into an infusion set 146 that is penetrated into the user's skin. In some examples, the user can temporarily detach reusable insulin pump controller 200 (while disposable insulin pump body 100 remains adhered to the skin) so as to view and interact with the user interface 220. In some embodiments, the pump assembly 15 can operate (during an open-loop mode, for example) to deliver insulin to the user by a predetermined schedule of basal dosages, manually selected bolus dosages, or a combination thereof. A basal rate of insulin can be delivered in an incremental manner (e.g., dispense 0.25 U every fifteen minutes for a rate of 1.0 U per hour) according to a previously scheduled delivery profile to help maintain the user's blood glucose level within a targeted range during normal activity, when the user is not consuming food items. The user may select one or more bolus deliveries, for example, to offset the blood glucose effects caused by food intake, to correct for an undesirably high blood glucose level, to correct for a rapidly increasing blood glucose level, or the like. In some circumstances, the basal rate delivery pattern may remain at a substantially constant rate for a long period of time (e.g., a first basal dispensation rate for a period of hours in the morning, and a second basal dispensation rate for a period of hours in the afternoon and evening). In contrast, the bolus dosages can be more frequently dispensed based on calculations made by reusable insulin pump controller 200 or the mobile computing device 60 (which then communicates to reusable insulin pump controller 200). For example, reusable insulin pump controller 200 can determine that the user's blood glucose level is rapidly increasing (e.g., by interpreting data received from continuous glucose meter 50), and can provide an alert to the user (via the user interface 220 or via the mobile computing device 60) so that the user can manually initiate the administration of a selected bolus dosage of insulin to correct for the rapid increase in blood glucose level. In one example, the user can request (via the user interface of mobile computing device 60) a calculation of a suggested bolus dosage (e.g., calculated at the mobile computing device 60 based upon information received from the user and from reusable insulin pump controller 200, or alternatively calculated at reusable insulin pump controller 200 and communicated back to the mobile computing device 60 for display to the user) based, at least in part, on a proposed meal that the user plans to consume.

A number of embodiments of the invention have been described. Nevertheless, it will be understood that various modifications may be made without departing from the spirit and scope of the invention. Accordingly, other embodiments are within the scope of the following claims.

What is claimed is:
1. A server system comprising:
an estimated personal inventory database indicating operational durable diabetes treatment devices and operational disposable diabetes treatment devices in the possession of a user; and
an inventory management system is operable to:
apply predictive analytics that track usage patterns and amounts of diabetes supplies in the estimated personal inventory database based on current and historical supply usage data for the user;

draw, by the application of the predictive analytics, an inference of an accuracy of the estimated personal inventory database, and when drawing the inference of the accuracy of the estimated personal inventory database, weight the inference based on an amount of time that the user views the estimated personal inventory database at a graphical user interface without making changes to the estimated personal inventory database, wherein the personal diabetes equipment management system ensures, via the weighted inference of accuracy of the estimated personal inventory database, continuity of diabetes treatment by providing for replacement of at least one durable diabetes treatment device and one or more disposable diabetes treatment devices based on monitoring the estimated personal inventory database.

2. The server system of claim 1, wherein the graphical user interface concurrently presents both the estimated personal inventory database and a virtual inventory for the user in a common view.

3. The server system of claim 2, wherein the virtual inventory comprises a list of diabetes supplies reserved for shipment to the user.

4. The server system of claim 2, wherein the graphical user interface represents the virtual inventory using data structures identifying details about inventory, the details including an SKU for the inventory, order number, shipment tracking information, and expected date of delivery.

5. The server system of claim 1, wherein the estimated personal inventory database is estimated in part based on a recommended usage pattern, a usage pattern particular to the user, an average usage pattern for typical users, and based on activities detected by the system.

6. The server system of claim 1, wherein the graphical user interface is configured to dynamically resize and reposition information and control features for modifying that information.

7. The server system of claim 6, wherein the information and control features are dynamically resized and repositioned depending on dynamically adjusted display parameters.

8. The server system of claim 1, wherein the server system is configured to collect a copay for a diabetes supplies service.

9. The server system of claim 1, wherein the server system is configured to begin a diabetes supplies service in response to a physician prescribing the diabetes supplies service with a fixed monthly cost set without regard to an expected usage rate.

10. The server system of claim 9, wherein the diabetes supplies service is prescribed using a form that includes a fear of hypoglycemia rating.

11. The server system of claim 1, wherein the server system is configured to store and track expiration dates of one or more diabetes supplies, and generate a report regarding use or accumulation of expired or unused diabetes supplies to determine a medication-therapy adherence score.

12. The server system of claim 1, wherein the server system is configured to provide a diabetes management system starter kit to the user.

13. The server system of claim 1, wherein the operational durable diabetes treatment device records an identifier of the operational disposable diabetes treatment device, and transmits the identifier to the server system, with a delay based on being of secondary importance as not relating to immediate health and safety of the user.

14. The server system of claim 1, further comprising a mobile computing device, wherein the operational durable diabetes treatment device transmits signals in real time to the mobile computing device, and wherein the mobile computing device aggregates information received from the operational durable diabetes treatment device before producing the information to the server system.

15. The server system of claim 1, wherein the graphical user interface comprises graphical display elements that include a list of disposable diabetes devices, a series of estimates of a number of each type of supply in the estimated personal inventory database, a number of items to be included in a next shipment in a virtual inventory, and an indication of a next shipping date.

16. The server system of claim 15, wherein the graphical user interface is configured for the user to add or change preferences for types of supplies to be delivered.

17. The server system of claim 1, wherein the graphical user interface includes a user selectable toggle switch to allow the user to update a number of each supply listed.

18. The server system of claim 1, wherein the inference is weighted based on factors indicating how closely the user analyzed estimates in the estimated personal inventory database.

19. The server system of claim 1, wherein the server system updates a virtual inventory based on changes to the estimated personal inventory database.

20. A method of providing durable diabetes treatment devices and supplies by a personal diabetes equipment management system, the method comprising:

tracking, by a computer system, use of at least one durable diabetes treatment device by a user to determine an operational condition for the at least one durable diabetes treatment device or one or more disposable diabetes treatment devices;

maintaining and updating an estimated personal inventory database for the user based on the tracking; and drawing an inference of an accuracy of the estimated personal inventory database, wherein the inference is weighted based on an amount of time that the user views the estimated personal inventory database at a graphical user interface without making changes to the estimated personal inventory database, wherein the personal diabetes equipment management system ensures, via the weighted inference of accuracy of the estimated personal inventory database, continuity of diabetes treatment by providing for replacement of at least one durable diabetes treatment device and one or more disposable diabetes treatment devices based on the tracking and the estimated personal inventory database.

* * * * *

UNITED STATES PATENT AND TRADEMARK OFFICE
CERTIFICATE OF CORRECTION

| | | |
|---|---|---|
| PATENT NO. | : 12,283,357 B2 | Page 1 of 1 |
| APPLICATION NO. | : 17/647112 | |
| DATED | : April 22, 2025 | |
| INVENTOR(S) | : Jeffrey Brewer et al. | |

It is certified that error appears in the above-identified patent and that said Letters Patent is hereby corrected as shown below:

On the Title Page

Item (73) Assignee, replace "BIIGFOOT" with --BIGFOOT--

Signed and Sealed this
Fourth Day of November, 2025

John A. Squires
*Director of the United States Patent and Trademark Office*